(12) United States Patent
Browning

(10) Patent No.: US 7,334,489 B2
(45) Date of Patent: Feb. 26, 2008

(54) DUAL RATE FORCE TRANSDUCER

(75) Inventor: Joel Seth Browning, Simi Valley, CA (US)

(73) Assignee: Custom Sensors & Technologies, Inc., Moorpark, CA (US)

( * ) Notice: Subject to any disclaimer, the term of this patent is extended or adjusted under 35 U.S.C. 154(b) by 0 days.

(21) Appl. No.: 11/363,405

(22) Filed: Feb. 27, 2006

(65) Prior Publication Data

US 2007/0034023 A1      Feb. 15, 2007

Related U.S. Application Data

(60) Provisional application No. 60/707,322, filed on Aug. 10, 2005.

(51) Int. Cl.
*G01N 22/00*    (2006.01)
*G01L 1/04*    (2006.01)

(52) U.S. Cl. .................................... 73/862.638; 73/161
(58) Field of Classification Search ........... 73/862.638, 73/161
See application file for complete search history.

(56) References Cited

U.S. PATENT DOCUMENTS

| | | | |
|---|---|---|---|
| 1,436,344 A | | 11/1922 | Hickey |
| 2,421,222 A | | 5/1947 | Schaevitz |
| 4,142,499 A | * | 3/1979 | Salzgeber ............... 123/339.29 |
| 4,148,469 A | * | 4/1979 | Geyer ............................ 267/4 |
| 4,186,914 A | * | 2/1980 | Radwill et al. ................. 267/4 |
| 4,375,243 A | | 3/1983 | Doll |
| 4,386,386 A | * | 5/1983 | Akita ....................... 361/283.1 |
| 4,423,793 A | | 1/1984 | Caris |
| 4,491,027 A | | 1/1985 | Yalof et al. |
| 4,500,768 A | * | 2/1985 | Rossell ..................... 219/86.25 |
| 4,632,198 A | | 12/1986 | Uchimura |
| 4,702,150 A | * | 10/1987 | Kaji ............................ 92/128 |
| 5,029,310 A | * | 7/1991 | Sakaida et al. ............. 396/584 |
| 5,072,799 A | | 12/1991 | Freeman et al. |
| 5,190,117 A | | 3/1993 | Freeman et al. |
| 5,628,477 A | * | 5/1997 | Caferro et al. ............... 244/214 |
| 5,925,832 A | | 7/1999 | Bruns |
| 6,708,803 B2 | * | 3/2004 | Jensen ........................ 188/275 |
| 6,827,401 B2 | * | 12/2004 | Marshall et al. .......... 297/302.1 |
| 6,871,549 B2 | * | 3/2005 | Serra et al. .................... 73/819 |
| 2005/0023047 A1 | | 2/2005 | Yoshikawa |
| 2005/0057033 A1 | * | 3/2005 | Ante .......................... 280/806 |

* cited by examiner

*Primary Examiner*—Max Noori
(74) *Attorney, Agent, or Firm*—Jeffer Mangels; Butler & Marmaro LLP

(57) ABSTRACT

A dual rate force transducer is disclosed. A spring is machined to have a first spring portion with a first spring rate, a second spring portion with a second spring rate, and a platen between the spring portions. A pair of flanges are affixed to the distal ends of the spring portions. At least one sensor is affixed to one of the flanges, and at least one other sensor is affixed to another one of the flanges. Mounting hardware is used to couple the springs, flanges and platen together, including at least one mechanical stop to limit displacement of the spring.

12 Claims, 7 Drawing Sheets

FCE (CHANNELS 1 & 2)

FDR (CHANNEL 3)

DUAL RATE FORCE TRANSDUCER

CROSS REFERENCE TO RELATED APPLICATION

This application claims priority from U.S. Provisional Application No. 60/707,322.

BACKGROUND OF THE INVENTION

This disclosure relates generally to measuring devices, and more particularly, to a force transducer that utilizes a one-piece machined spring to provide two different spring rates and multiple sensors to measure the different rates.

In the prior art, two separate force transducers are used to measure two different force ranges. This requires separate mounting schemes for each transducer, which adds mechanical complexity and weight to the overall hardware scheme.

BRIEF SUMMARY OF THE INVENTION

A dual rate force transducer includes a dual rate spring coupled between opposing members. One portion of the spring has a first spring rate, and another portion of the spring has a second spring rate. Multiple sensors are coupled to measure spring displacement. A mechanical stop is used to limit compression of the spring.

BRIEF DESCRIPTION OF THE DRAWINGS

The described embodiment(s) may be more readily understood by referring to the accompanying drawings in which.

Like numerals refer to like parts throughout the several views of the drawings.

DETAILED DESCRIPTION OF THE INVENTION

The preferred embodiment described herein is a dual rate force transducer. A dual rate spring is provided by machining a single piece of material (such as stainless steel) to have two different tension specifications on either end of the spring, with a shared flange or platen between the spring portions. Another flange is affixed on the distal end of each spring portion. Multiple LVDTs are mounted with the spring to measure displacement. For example, in the preferred embodiment, the LVDT transformers are affixed to the center, shared flange, while the moveable cores (armatures) are affixed to either one of the end flanges. The signals from all LVDT's are coupled to a signal processing circuit where they are processed and used for detection and control schemes.

Figure 1A:
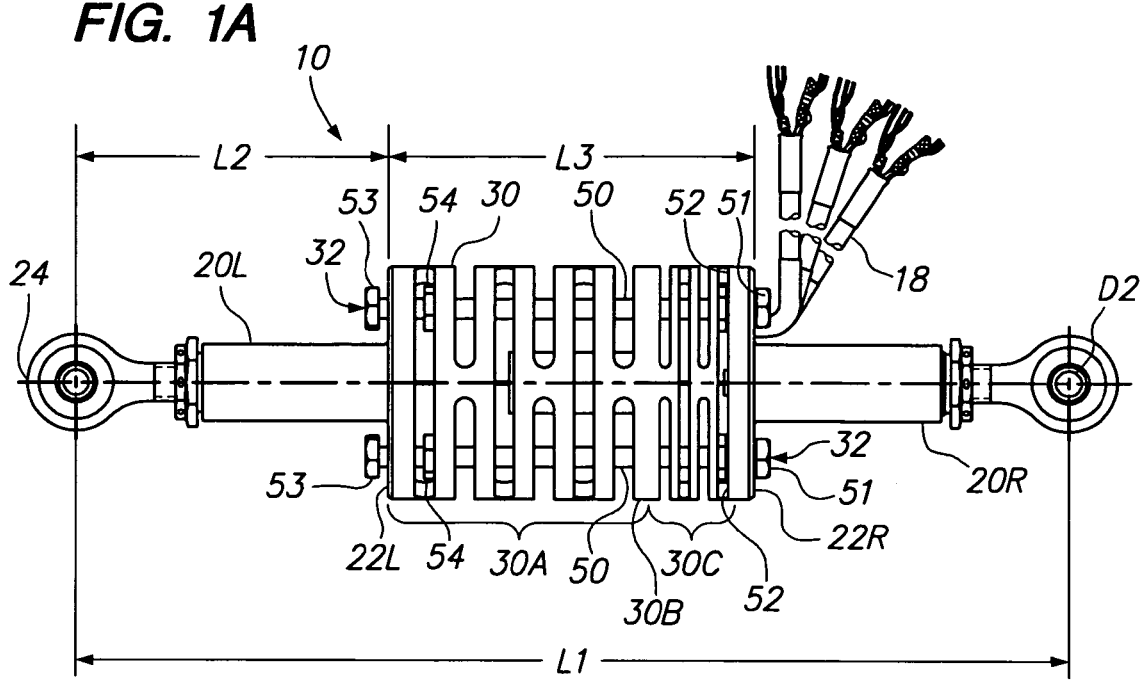
FIGS. 1A and 1B are plan views of a force sensor in accord with a preferred embodiment.
Figure 1B:
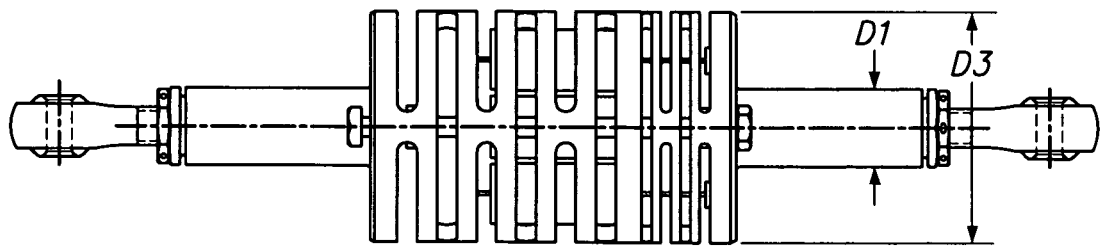

As illustrated schematically in FIGS. 1A and 1B, a force transducer 10 includes a pair of opposing strut portions 20L, 20R and a spring 30 mounted between the strut portions. The force sensor 10 is typically used for aircraft applications and is ideal for cockpit control applications, including sensing the forces applied by a pilot to the aileron, elevator, and rudder controls. The strut portions 20L, 20R have flange portions 22L and 22R formed on the near ends of the strut portions. In one preferred embodiment, a stop rod 32 is coupled between the flange portions 22L, 22R and is used to limit the compression/retraction and expansion/extension of the spring 30 so that the spring is protected from the full limits and ultimate force loads of the system. Specifically, the spring 30 may become deformed or fractured if (i) it is allowed to move through an unlimited range of travel during extension or retraction, or (ii) it experiences the full amount of force loads as applied to the strut portions 20L, 20R.

Figure 2:
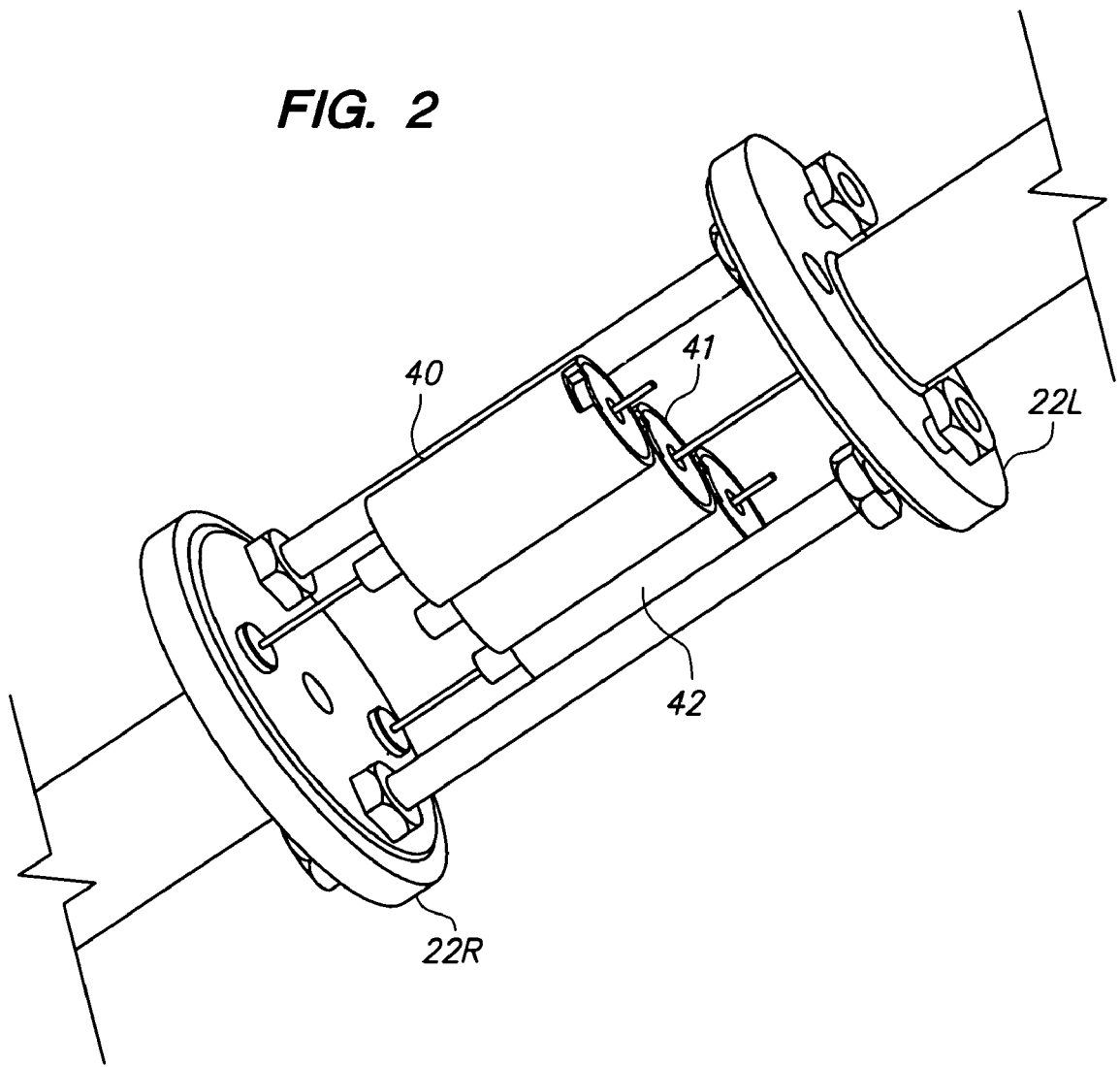
FIG. 2 is a perspective view of a force sensor with the spring omitted to show the LVDTs.

Mounted for operation inside the spring 30 are three linear variable differential transformers (LVDTs) 40, 41, and 42, as shown in FIG. 2. An LVDT is a well known displacement measuring device that produces an electrical signal which is proportional to the displacement of a movable core (armature) within a cylindrical transformer. A full description thereof is considered unnecessary for the understanding of the present disclosure.

The construction of the strut portions 20L, 20R is also generally well known. Preferably, the struts are cylindrical in shape and machined from stainless steel or aluminum to have a diameter D1 of 0.750 inches. (All dimensions indicated in this disclosure are approximate.) The attachment portions 24 of the struts have a circular opening with diameter D2 of 0.2500 inches and are connected at one end of the sensor to a fixed position and at the other end of the sensor to the load of interest. The flange portions 22L, 22R are also made of stainless steel or aluminum with a diameter D3 of approximately 2.25 inches and are fixed to the struts by weldment, for example. The total length L1 of the sensor in the null position is 9.5 inches, with each of the strut portions having a length L2 measuring 3.00 inches and the spring portion having a length L3 measuring 3.50 inches.

Figure 3A:
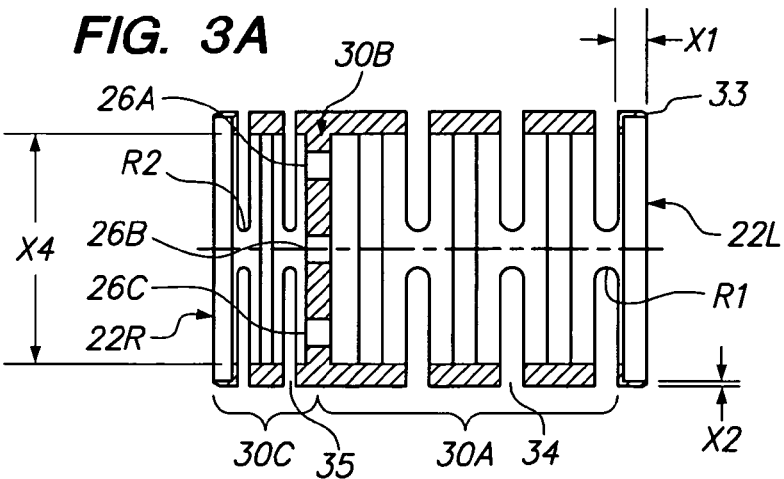
FIGS. 3A-3E are plan views of the spring and flange.
Figure 3B:
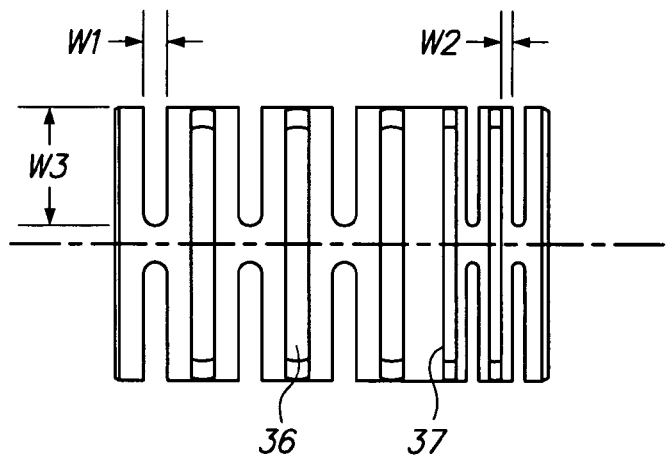
Figure 3C:
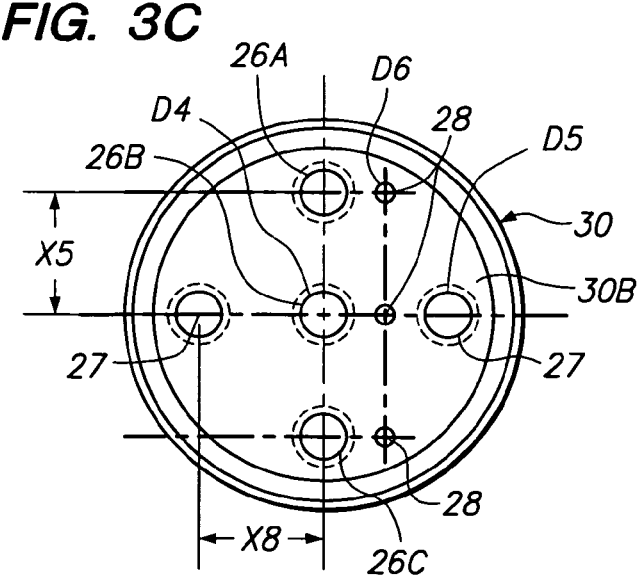

A detailed illustration of the preferred embodiment of spring 30 is shown in FIGS. 3A-3C. The spring 30 is preferably machined from a single piece of 15-5 PH stainless steel per aerospace material specification ("AMS") 5659, in a solution heat treated condition, to have a cylindrical configuration. Beginning at the right side of FIG. 3A, the spring 30 includes an annular portion 33 with a depth X1 of approximately 0.252 inches and a thickness X2 of approximately 0.003 inches, into which the flange 22L is mounted. In one preferred embodiment, the flange 22L is welded in place. The left side of the spring 30, as illustrated in FIG. 3A, has a similar annular portion for the mounting of the flange 22R. The ends of stop rods 32 pass through corresponding flange openings 127 in flanges 22L, 22R, respectively. As seen in FIGS. 1A and 3A, the spring 30 includes two different rate portions, namely a Flight Data Recorder (FDR) portion 30a and a Flight Control Electronic (FCE) portion 30c, separated by a spring division flange 30b. The FDR portion 30a and FCE portion 30c of spring 30 effectively create two springs that react to the forces applied to the control system during the engagement of the FDR and FCE, respectively.

Generally, using well known design criteria, the spring is made up of beams that are offset from each other by 90°. The thickness of the beams is what gives the spring its spring rate by bending under a given load. The thickness of the beams is varied in order to produce different spring rates that are particular to any given application. The gaps or slots 34, 35, 36 and 37 between the beams are dictated by the thickness of the beam and the overall length of the spring. This type of force transducer would typically be used in a situation that requires two force ranges, one much larger than the other, that would typically require two separate transducers to achieve the range and accuracy requirements. Each spring can have its spring rate (the thickness of the beams) tailored to a single force range without affecting the range of the other spring. For a given force and number of cycles, each spring must be able to withstand the stresses without suffering a fatigue failure. With this in mind, the stops are utilized to make sure neither spring ever sees a force that is beyond its operating range.

While it is preferred that the spring and division flanges be machined from a single piece of stock, it is possible to machine two individual springs and then connect them, for example by welding or brazing, to a common division flange. Further, a single spring having dual rates could be machined without a central flange, and the flange could be added later, for example, by pins or welding.

In this preferred embodiment, a series of three slotted portions 34 are formed between beams in the spring FDR portion 30a of 30, each having a depth X3 of 2.2 inches and an inside radius of curvature R1 of 0.095 inches. The width W1 of slots 34 is 0.190 inches. Two smaller slotted portions 35 are formed in the FCE portion 30c of spring 30, each having the same depth X3 as slots 34, an inside radius R2 of 0.055 inches, and a width W2 of 0.070 inches. The edges of the slots 34, 35 should be broken inside and outside around a radius blend of 0.010 to 0.030 inches or 0.005 to 0.030 times 45 degrees plus or minus a 10 degree chamfer. Further, there should be no machine marks on any of the inside radii of the slots or on the outside surface of the spring.

A series of three gaps 36 and two gaps 37 are also formed in the spring 30. The first set of gaps 36 has the same width W1 as slots 34, and the second set of gaps 37 has the same width W2 as slots 35. The depth X4 of gaps 36, 37 is 1.950 inches. It can be seen that the slots 34, 35 and the gaps 36, 37 are interleaved openings that allow for a small degree of compression of the spring 30.

As shown in FIG. 3C, the spring division flange 30b of spring 30 has a series of openings. Three openings 26A-C each having a diameter D4 of 0.3125 inches are provided to receive a mounting for the transformer portion of the LVDT (not shown), as described below. One of the openings 26B is positioned in the center of the flange, and the other two openings 26A, 26C are positioned in line with the center opening at a distance X5 of 0.719 inches from the center opening. Two openings 27 each having a diameter D5 of 0.250 inches are positioned at a distance X8 of 0.650 inches from the center opening 26. Openings 27 are provided for stop rod 32 to insert therethrough. Three openings 28 each having a diameter D6 of 0.138 inches are provided to receive conductors 18 from the LVDTs located inside the spring 30.

Figure 3D:
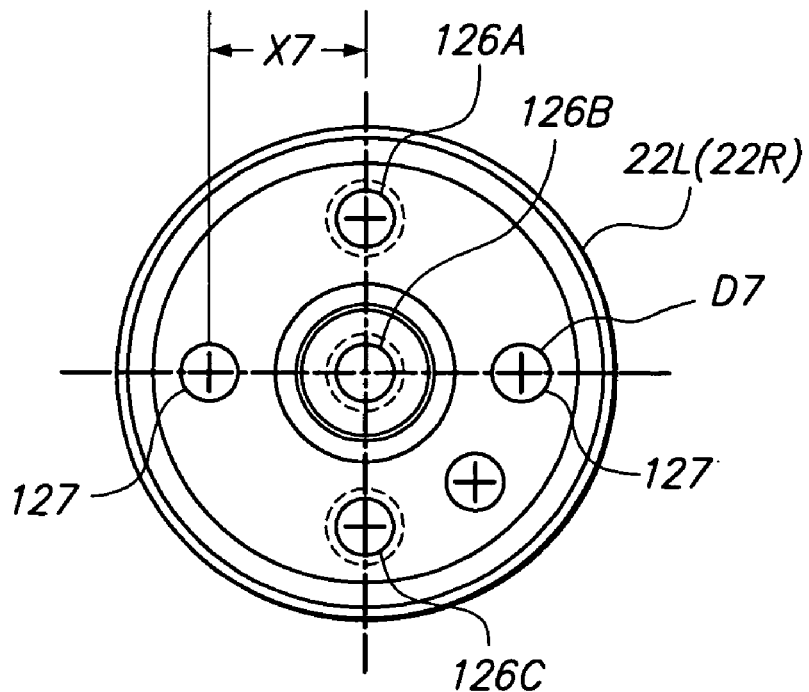
Figure 3E:
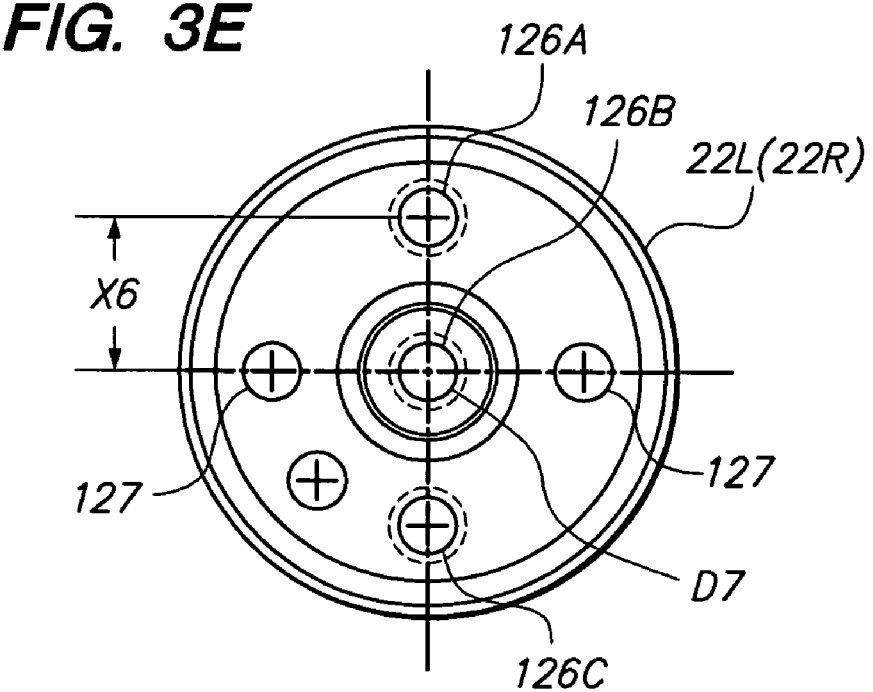

As shown in FIGS. 3D-E, flange 22L (and similarly flange 22R, not shown) has a series of openings. Three openings 126A-C each having a diameter D7 of 0.3125 inches are provided to receive a mounting for the metal core of the LVDT (not shown), as described below. One of the openings 126b is positioned in the center of the flange, and the other two openings 126A, 126C are positioned in line with the center opening 126b at a distance X6 of 0.719 inches from the center opening 126b. Two openings 127 each having a diameter D7 of 0.250 inches are positioned at a distance X7 of 0.650 inches from the center opening 126b. Openings 127 are provided for stop rod 32 to insert therethrough.

Figure 4:
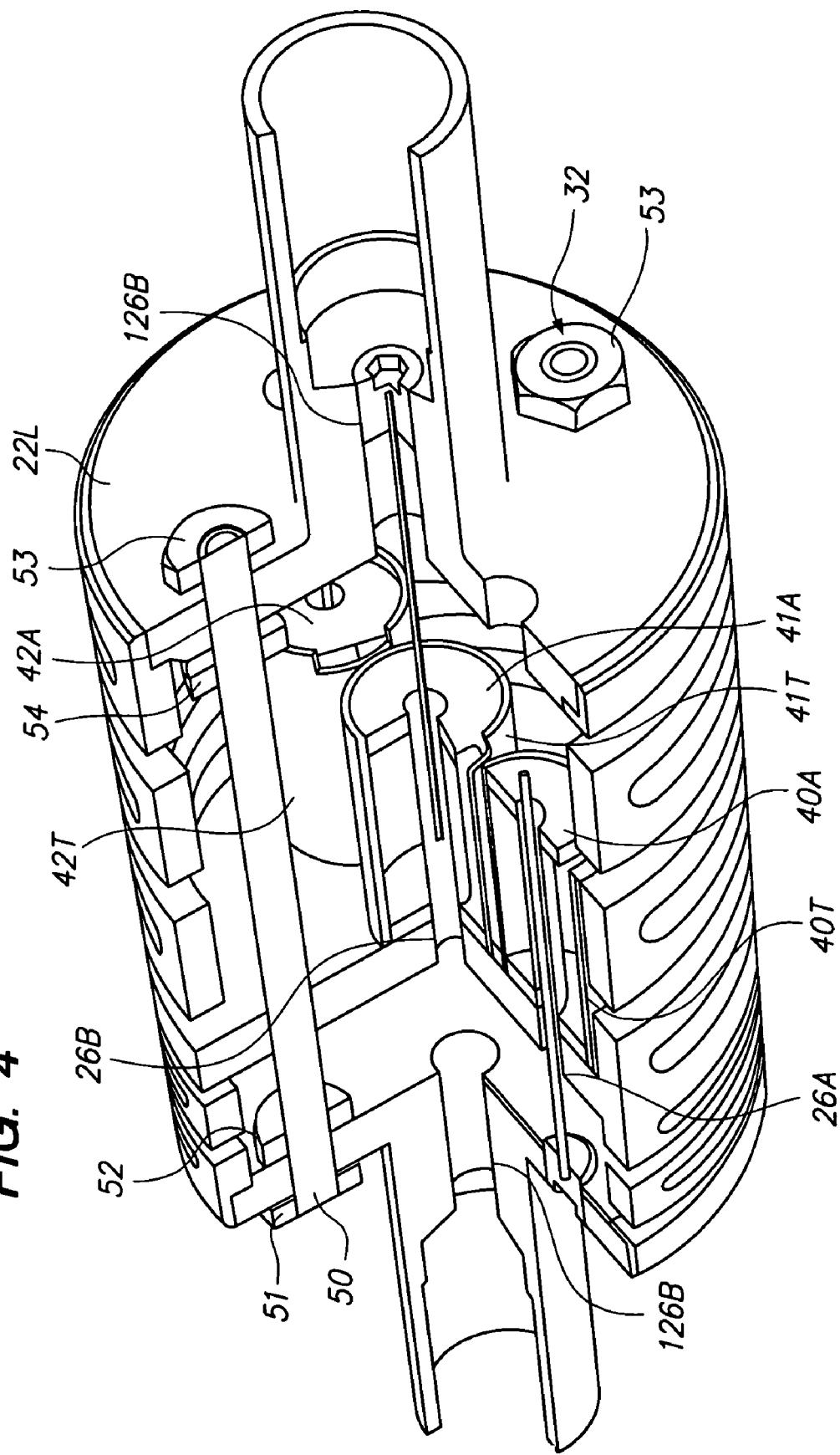
FIG. 4 is a perspective view of a force sensor with a portion of the spring cut away to show the LVDTs.

Referring now to FIG. 1A and FIG. 4, it can be seen that stop rod 32 includes a pair of threaded rods and locking nuts fitted through openings 27. Specifically, stop rod 32 includes a pair of threaded rods 50, which are fitted through corresponding openings 27 of the spring division flange 30b in spring 30 and also through corresponding openings 127 in flange 22L and flange 22R. Near flange 22L, locking nut 53 is fixed to the threaded rod 50 in a position that is offset outboard of flange 22L to provide a mechanical stop for the extension of the FDR portion 30a of the spring 30. Likewise, locking nut 54 is fixed to the threaded rod 50 in a position that is offset inboard of the flange 22L to provide a mechanical stop for the FDR portion 30a of the spring 30. Similarly, near the flange 22R, locking nuts 51 and 52 are fixed to threaded rod 50 to provide mechanical stops against extension and retraction, respectively, of the FCE portion 30c of spring 30 from flange 22R. The stop engagement point of the FCE portion 30c of spring 30 is 0.020 inches from its no load position and the stop engagement point of the FDR portion 30a of the spring 30 is 0.090 inches from its no load portion. The stop rod specification is dictated by the limit and ultimate loads. The material and/or size of the rod must be able to withstand the loading that will occur for the unit without buckling. The compression load will be the limiting factor and not the tensile loading. Taking into account the length of the rod and its limited support at the guided end where it goes through the flanges, 22L and 22R, the force applied through the nut must be analyzed by a column method to assure that the rods have a large enough safety margin to support the limit and ultimate loads. The stop rod used can be from standard threaded rod stock, but the size must be chosen according to the stress analysis. And similarly, the material of the threaded rod can be changed to an exotic material to achieve a stronger rod and provide a smaller package. The nut would typically be a standard off-the-shelf type of jam nut, but could be any shape that would serve the intended function of supporting the flange load. It is also optional to have one, two or as many stops as wished, however, two is probably the preferred configuration to allow a higher safety margin with a minimum of adjustment of the individual rods needed.

Figure 5A:
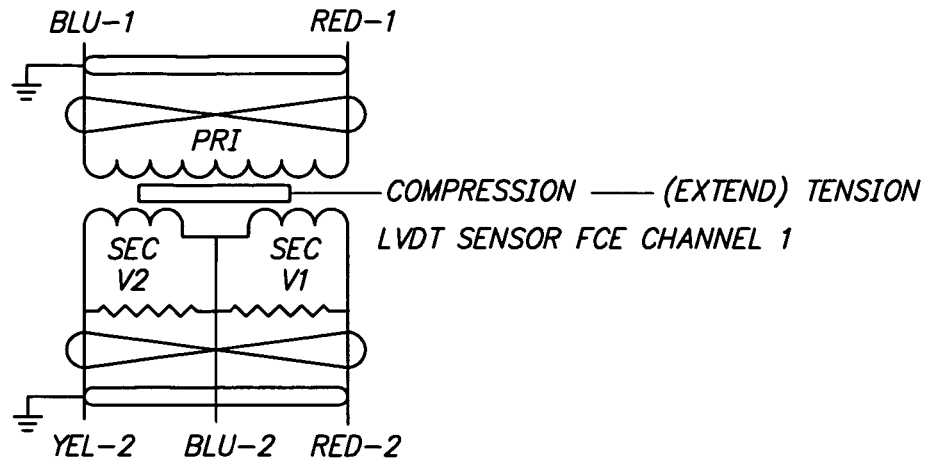
FIGS. 5A-5C are electrical schematics for the LVDTs.
Figure 5B:
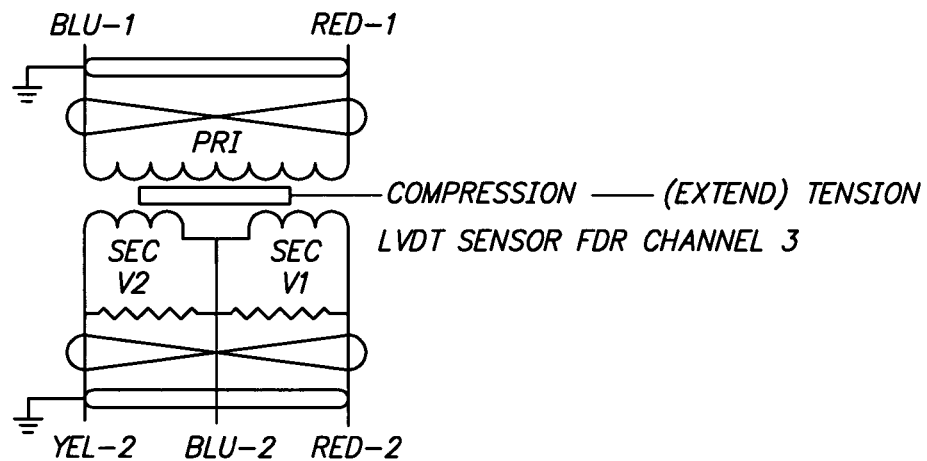
Figure 5C:
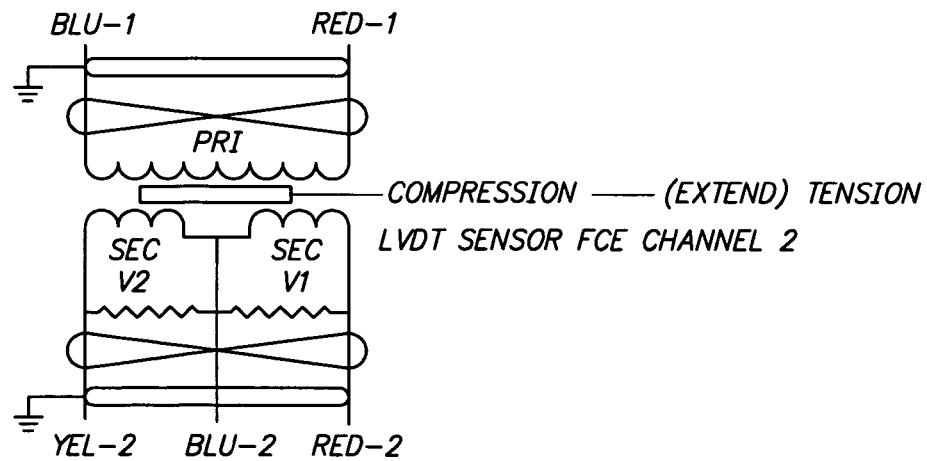
Figure 6A:
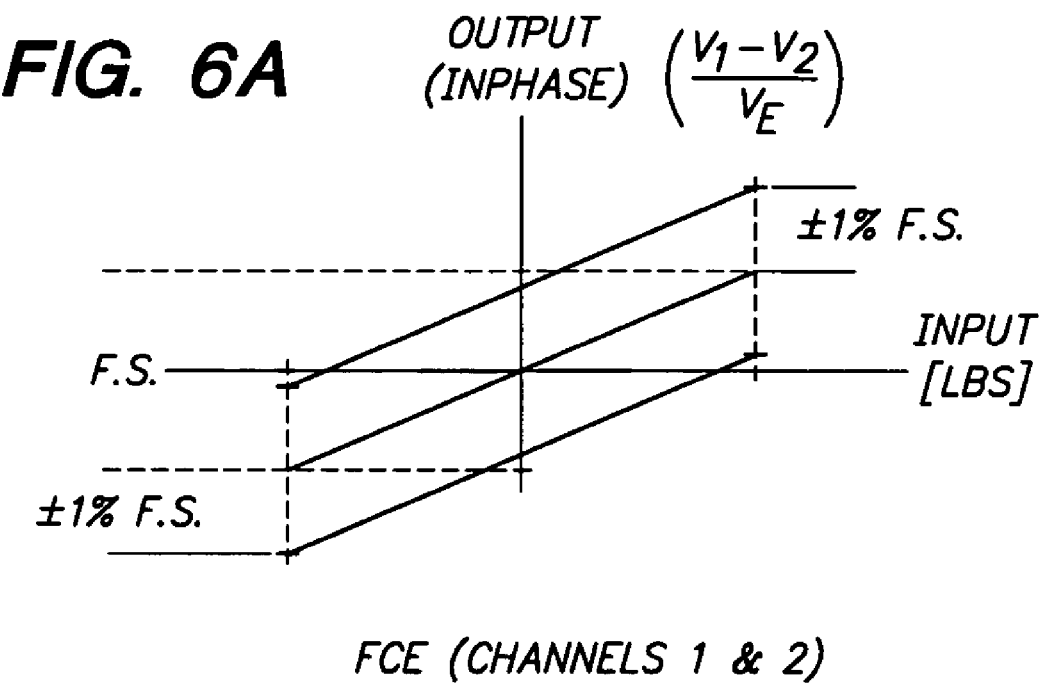
FIGS. 6A-6B are graphs of input force versus output deviation.
Figure 6B:
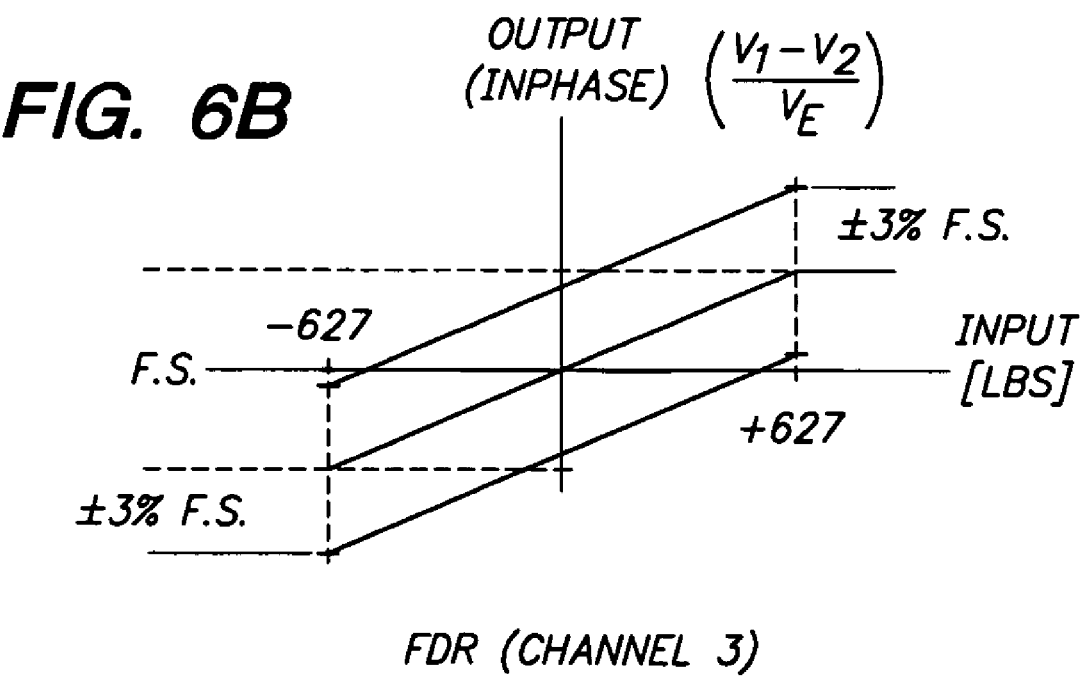

Referring now to FIG. 2 and FIG. 4, LVDT 41 has its transformer portion 41T fixed in position within spring 30 with respect to the center opening 26b on the spring division flange 30b and the movable core 41A is fixed to the flange 22L with respect to the center opening 126b. Likewise, LVDT 40 has its transformer portion 40T fixed in position within spring 30 with respect to opening 126A on spring division flange 30b and the movable core 40A is fixed to the other flange 22R with respect to end opening 126A. LVDT 42 is configured in the same way as LVDT 40 such that its transformer portion 42T is fixed with respect to opening 26 in spring division flange 30b in spring 30 and its movable core 42A is fixed with respect to opening 126A of flange 22R. Thus, the two outer LVDTs 40, 42 have their movable core fixed to flange 22R while the center LVDT 41 has its movable core fixed to flange 22L. The electrical schematics for each of the LVDTs are provided in FIGS. 5A-5C. The output characteristic for the FCE portion 30c of spring 30 is illustrated in FIG. 6A, where channels 1 and 2 (LVDTs 40 and 42) are summed in phase. The output characteristic for the FDR portion 30a of spring 30 is illustrated in FIG. 6B, where channel 3 (LVDT 41) is measured.

It is noted that foregoing description is a preferred embodiment, but dimensions and measurements are approximate. In general, a sensor constructed according to this description can be used to measure a full scale range of ±627 lbs, with a load limit of ±1450 lbs and an ultimate limit of ±2175 lbs. The spring rate for extension FCE is 1000±10% lbs/inch, and the spring rate for retraction FDR is 7000±10% lbs/inch.

The electrical specifications are given in Table I.

TABLE I

| EXCITATION | | |
| --- | --- | --- |
| Voltage | 7.07 VRMS ± 5.0% | |
| Frequency | 1800 ± 50 Hz | |
| Waveform | Sine | |
| Power | 0.15 V.A. max/channel | |
| INPUT IMPEDANCE | 400 Ω min. | |
| OUTPUT IMPEDANCE | 1500 Ω max | |
| LOAD | [each half] | [entire sec] |
| Resistive | 36 ± 20% kΩ | 42 ± 20% kΩ |
| Capacitive | 3300 ± 20% pF | none |
| DIELECTRIC STRENGTH | | |
| Coil to Coil | 750 VRMS, 60 Hz (1 min) | |
| Coil to Case | 750 VRMS, 60 Hz (1 min) | |
| INSULATION RESISTANCE | 100 MΩ min @ 500 VDC | |
| BONDING RESISTANCE | 15 MIL Ω (@ 1 amp) | |
| PHASING | with RED-1 common with BLU-2, BLU-2 shall be in phase with YEL-2 & RED-2 over the entire range and the voltage V1 from BLU-2 to RED-2 shall increase in tension | |

The performance specifications are given in Table II.

TABLE II

| SENSITIVITY | 0.00294 V/V/lb |
| --- | --- |
| TEMPERATURE COEFF. | 1.5%/100° F. (local value) |
| ACCURACY | per FIGS. 6A & 6B |
| PHASE SHIFT | 15 |
| HYSTERESIS | 0.5% F.S. max |

Although a specific embodiment has been described, it will be evident that various modifications and changes may be made to this embodiment without departing from the spirit and scope of the invention. Accordingly, the specification and drawings are to be regarded as illustrative rather than restrictive. The proper scope of the invention is defined by the accompanying claims.

I claim:

1. A dual rate force sensor, comprising a pair of opposing members having a dual rate spring coupled therebetween, a mechanical stop that provides a physical limit for spring displacement both in a tension direction and a compression direction, and a plurality of sensors mounted in close proximity to the spring and adapted to measure spring displacement.

2. A dual rate force sensor as in claim 1, wherein the dual rate spring is precision machined from a single piece of stock to have a first spring portion with a first spring rate, a second spring portion with a second spring rate, and a platen fixed between proximate ends of the first and second spring portions.

3. A dual rate force sensor as in claim 1, wherein each sensor has a fixed transformer and a movable core, with at least one of the sensors having its movable core coupled to one opposing member and at least one of the sensors having its movable core coupled to the other opposing member.

4. A dual rate force sensor as in claim 1, wherein the sensors are coupled to a signal processing circuit.

5. A dual rate force transducer, comprising:
a pair of struts each having a flange on a proximal end thereof;
a spring mounted to the flanges between the struts and having a first portion with a first spring rate, a second portion with a second spring rate, and a platen fixed between proximate ends of the first and second portions, wherein a first end of the spring is coupled to one flange and a second end of the spring is coupled to the other flange; and
a plurality of displacement sensors coupled proximate to the spring, each sensor having a fixed transformer and a movable core, with at least one of the sensors having its movable core coupled to the one flange and at least one of the sensors having its movable core coupled to the other flange.

6. A dual rate force transducer as in claim 5, wherein the spring is precision machined from a single piece of stock.

7. A dual rate force transducer as in claim 5, further comprising a mechanical stop that provides a physical limit for spring displacement.

8. A dual rate force sensor, comprising
a first spring having a first spring rate;
a second spring having a second spring rate;
a first and a second flange each positioned at a distal end of the first and second springs, respectively;
a third flange coupling a proximate end of the first spring to a proximate end of the second spring;
mounting hardware coupled through the first, second and third flanges; and
a plurality of force sensors mounted proximate to the first and second springs and adapted to measure spring displacement.

9. A dual rate force sensor as in claim 8, wherein the first spring, second spring, and third flange are precision machined from a single piece of stock.

10. A dual rate force sensor as in claim 8, wherein each displacement sensor has a fixed transformer and a movable core, with at least one of the sensors having its movable core coupled to the first flange and at least one of the sensors having its movable core coupled to the second flange.

11. A dual rate force sensor as in claim 8, wherein the mounting hardware includes a mechanical stop that provides a physical limit for spring displacement.

12. A dual rate force transducer, comprising
a dual rate spring machined from a single piece of stock to have a first spring portion with a first spring rate, a second spring portion with a second spring rate, and a platen fixed between proximate ends of the first and second spring portions;
a first flange and a second flange each coupled to a distal end of the first spring portion and the second spring portion, respectively;
mounting hardware coupled through the flanges and the platen including a mechanical stop to provide a physical limit for spring displacement; and
a plurality of displacement sensors mounted within the spring, at least one of said sensors being coupled to the first flange and at least one other of said sensors being coupled to the second flange.

* * * * *